United States Patent [19]
Mason et al.

[11] Patent Number: 5,877,223
[45] Date of Patent: Mar. 2, 1999

[54] NATURALLY-OCCURRING ODORIFEROUS ANIMAL REPELLENT

[75] Inventors: James Russell Mason, Bridgeton, N.J.; Richard Albert Dolbeer, Huron, Ohio; George Preti, Horsham, Pa.

[73] Assignee: Monell Chemical Senses Center, Philadelphia, Pa.

[21] Appl. No.: 490,760

[22] Filed: Mar. 8, 1990

Related U.S. Application Data

[63] Continuation-in-part of Ser. No. 394,932, Aug. 17, 1989, abandoned, which is a continuation-in-part of Ser. No. 351,841, May 12, 1989, abandoned.

[51] Int. Cl.$^6$ ..................................................... A61K 31/12
[52] U.S. Cl. ........................................... 514/690; 424/581
[58] Field of Search .............................. 424/581; 514/690

[56] References Cited

U.S. PATENT DOCUMENTS

| | | | |
|---|---|---|---|
| 3,474,176 | 10/1969 | Freeman . | |
| 3,882,248 | 5/1975 | Igimi et al. . | |
| 3,923,997 | 12/1975 | Meuly | 424/279 |
| 4,169,898 | 10/1979 | Haase et al. | 424/331 |
| 4,169,902 | 10/1979 | De Long | 427/4 |
| 4,320,112 | 3/1982 | Jones et al. | 514/703 |
| 4,414,227 | 11/1983 | Tomlinson . | |
| 4,440,783 | 4/1984 | Downing | 424/302 |
| 4,534,976 | 8/1985 | Hansen et al. | 514/169 |
| 4,555,015 | 11/1985 | Haase | 206/0.5 |
| 4,656,038 | 4/1987 | Baugh | 424/164 |
| 4,657,759 | 4/1987 | Hansen et al. | 424/83 |
| 4,668,455 | 5/1987 | Hansen et al. | 264/143 |
| 4,735,803 | 4/1988 | Katz et al. | 424/195 |
| 4,775,532 | 10/1988 | Clayton | 424/195.1 |

OTHER PUBLICATIONS

Dolbeer, R.A., et al., "Naphthylene shows no repellency for starlings", *Wildlife Society Bulletin*, 16:62–64 (1988).

Seamans, T., et al., "Allyl isothiocyanate (oil of mustard) as a starling repellent", Denver Wildlife Research Center, Bird Section Research Report #408, 10 pp.

Mason, R., "Evaluation of d–pulegone as an avian repellent", *J. Wildlife Management*, vol. 54, No. 1, pp. 130–134 (1990).

Inazuka et al., Monterpenoids as Repellents Against the German Cockroach (*Blatella germanica* L), CA100:116461, 1984.

Schafer, E.W., et al., in "The Acute Oral Toxicity, Repellency and Hazard Potention of 998 Chemicals to One or More Species of Wild and Domestic Birds", *Archives of Environmental Contamination and Toxicology*, 12:355–382 (1983).

Mason, J.R., et al., The effectiveness of six potential irritants on consumption by red–winged blackbirds (*Agelaius phoeniceus*) and starlings (*Sturnus vulgaris*). In Green, B., Mason, J.R. and Kare, M.R., Chemical Irritation in the Nose and Mouth, Marcel Dekker, NY, NY, in press.

Szolcsanyi et al., "Nociception in pigeons is not impared by capsaicin", *Pain*, 27:247–260 (1989).

*Primary Examiner*—Jean C. Witz
*Attorney, Agent, or Firm*—Woodcock Washburn Kurtz MacKiewicz & Norris, LLP

[57] ABSTRACT

Certain volatile compounds naturally present in herring gull eggs are effective for repelling animals and birds, particularly canids, from the locus to which such compounds are applied. More particularly, the volatile compounds which are effective animal repellents include compounds exhibiting mint-like odors such as the compounds pulegone and piperitone. The invention relates to methods of using these compounds to repel animals, and to repellent compositions comprising effective repellent amounts of such compounds.

19 Claims, No Drawings

NATURALLY-OCCURRING ODORIFEROUS ANIMAL REPELLENT

RELATED APPLICATIONS

This application is a continuation-in-part of U.S. application Ser. No. 394,932, filed on Aug. 17, 1989, now abandoned, which is in turn a continuation-in-part of U.S. application Ser. No. 351,841, filed on May 12, 1989, now abandoned.

BACKGROUND OF THE INVENTION

This invention relates to methods of repelling animals and birds, especially canines. More particularly, the invention relates to the use of volatile compounds exhibiting a mint-like odor, such as pulegone and piperitone, to repel animals and birds.

It is often advantageous to discourage animals from frequenting certain areas. Any homeowner who has ever had to pick up garbage strewn from a trash receptacle or bag by a neighborhood dog will attest to the desirability of discouraging the animal from such activity. It may also be desirable to keep animals away from certain areas such as ornamental or agricultural plantings, to which they can cause damage, or from areas in which the animals could themselves be injured. In addition, many domestic pets are injured or killed each year by accidental ingestion of harmful substances, such as the antifreeze which can leak from automobiles, and a way to prevent such accidents would be of great use.

Numerous chemical agents have been used over the years to discourage animals from approaching those areas from which mankind finds it desirable to exclude them. For obvious reason, such chemical agents should not only be effective for repelling the animals, but, if they are to be used in populated areas, should be acceptable to humans in terms of safety and odor.

The compounds undecanone-2, commonly known as methyl nonyl ketone, and 3-phenylpropenal (common names: cinnamaldehye or beta-phenylacrolein), have been disclosed as animal repellents, and their use together in a synergistic mixture is disclosed in U.S. Pat. No. 4,169,898 (Haase et al.). U.S. Pat. No. 4,555,015 (Haase) discloses that the animal repellent methyl nonyl ketone has the ability of being applied to a comparatively small surface area of a plastic to migrate to a comparatively large area of a plastic surface even to the extent of migrating to the opposite surface of a plastic film. Thus, the compound may be applied to a comparatively small area of the inside surface of a plastic bag, after which the bag is folded upon itself at least once (e.g., when it is placed in a package of a plurality of such bags), and the repellent will migrate over comparatively large areas inside and outside of said bag.

A composition containing as its active ingredient an allyl isothiocyanate (mustard oil) or the alkyl derivatives thereof, is disclosed in U.S. Pat. No. 4,440,783 (Downing) as being useful for repelling animals such as raccoons, dogs and the like from garbage while at the same time being non-toxic and non-repellent to humans. Interestingly, this patent states (column 1, line 31) that peppermint oil has not been used effectively for repelling animals.

Animal control compositions comprising lemon oil and alpha-terpinyl methyl ether, taken alone or taken together with quinine or salts thereof, are disclosed in U.S. Pat. No. 4,735,803 (Katz et al.).

U.S. Pat. No. 4,169,902 (De Long) discloses a method for repelling animals and birds consisting of applying to an area being protected a composition consisting essentially of an aqueous solution or dispersion of a carboxylated hydrophilic acrylic copolymer, a crosslinking agent for the carboxylated hydrophilic copolymer, a stabilizingly effective amount of an ultraviolet absorbing agent, and an animal or bird repelling compound.

A composition of matter for repelling animals comprising the mixture of a metallic metal, a quantity of a soil that has been extracted from the earth, a nutrient source and water is disclosed in U.S. Pat. No. 4,656,038 (Baugh).

A method for repelling animals from areas to be protected by use of a composition comprising a δ-n-alkyl-δ-butyrolactone and/or a δ-n-alkyl-δ-valerolactone is disclosed in U.S. Pat. No. 3,923,997 (Meuly).

U.S. Pat. Nos. 4,534,976, 4,657,759 and 4,668,455 (Hansen et al.) disclose that particular steroids may be used as key ingredients in animal repellent compositions.

U.S. Pat. No. 4,775,532 (Clayton) discloses that olfactory animal repellents can be effectively transported over surfaces by means of a vehicle comprising a liquid di(alkyl) adipate, i.e., esters of adipic acid, alone or in combination with a sodium di-$C_4$–$C_{13}$ alkylsulfosuccinate. The animal repellents disclosed for use with such vehicles include cinnamic aldehylde, methyl nonyl ketone, essence of red pepper and quinine.

SUMMARY OF THE INVENTION

It has now been found that certain naturally occurring, volatile, odoriferous compounds can be used to effectively repel carnivorous and omnivorous animals and birds, particularly canines, and more particularly dogs. These compounds have been found in herring gull eggs and may act to repel egg predators. This invention therefore relates to a method of repelling carnivorous and omnivorous animals comprising applying to the locus from which said animals are to be repelled an effective repellent amount of such naturally occurring, volatile, odoriferous compounds. The volatile compound is referably selected from compounds found in herring gull eggs and, more preferably, from the group consisting of compounds having mint-like odors such as pulegone and piperitone. This invention further relates to animal repellent compositions comprising an effective repellent amount of at least one such volatile compound and a suitable vehicle.

BRIEF DESCRIPTION OF THE DRAWINGS

FIGS. 1a and 1b are, respectively, the computer reconstructed gas chromatographic recordings for the volatile compounds collected from the headspace above samples of herring gull eggs and chicken eggs. The areas designated by the rectangle indicate the portion of the chromatograms where the two samples differed quantitatively.

FIGS. 2a and 2b are, respectively, expanded versions of the areas of the chromatograms of FIGS. 1a and 1b designated by the rectangles. The shaded components are those which differed qualitatively from chicken egg components (via mass spectrometry).

DETAILED DESCRIPTION OF THE INVENTION

Tests by the present inventors suggest that the compounds pulegone (1-isopropylidene-4-methyl-2-cyclohexanone) and piperitone (3-methyl-6-[1-methylethyl]-2-cyclohexen-1-one) are effective as repellents for carnivorous and omnivorous animals and birds. It is believed that the repellency of the compounds is due to their volatile nature, and that the compounds stimulate chemosensory systems in the nose. These systems are: olfaction, trigeminal chemoreception, vomeronasal chemoreception, septal organ chemoreception and terminal nerve chemoreception. Both pulegone and piperitone have mint or spearmint-like odors (the term "mint-like" being used herein to denote either type odor), and it is believed that other substances with these organoleptic qualities will also be useful as animal repellents. These compounds are particularly useful as animal repellents in view of the fact that their "mint-like" odors are not offensive to humans.

The tests of the present inventors have shown that the compounds are repellent to dogs. As such, it is expected that the compounds may also be used as a repellent for carnivorous (animal prey) and omnivorous (vegetable or animal prey) animals and birds, including domestic cats, rodents, racoons and other canids such as coyotes.

The method of this invention comprises applying an effective repellent amount of the volatile compound, either alone or in combination with a suitable carrier, to the locus from which the animals are to be repelled. Suitable carriers would include liquid diluents such as water, hydrocarbons, alcohols, emulsifiers and other liquids generally found in household spray formulations or pharmaceutical preparations so as to be acceptable from a human safety viewpoint. Inert solid carriers such as starches may also be of use, and it might be desirable to incorporate the compounds into a controlled-release formulation.

It may be desirable to apply the volatile mint-like compounds to containers for discarded edible refuse, such as metal or plastic garbage cans, plastic bags, paper and cardboard boxes and the like. One way to accomplish this would be according to the teachings of U.S. Pat. No. 4,775,532 (Clayton), the disclosure of which is hereby incorporated by reference. As previously indicated, U.S. Pat. No. 4,775,532 teaches that olfactory animal repellents can be effectively transported over surfaces by means of a vehicle comprising a liquid di(alkyl)adipate.

Since the tests of the present inventors have suggested that the repellent qualities of the compounds piperitone and pulegone are not lost upon heating of those compounds, it should be possible to incorporate the compounds into polymers for use in making functional articles containing the compounds, for example, animal-repellent garbage bags or receptacles.

Finally, the repellent compounds disclosed herein might be incorporated into various potentially-edible compositions which, if consumed, could injure or kill an animal. An example of such a composition would be liquid antifreeze.

The present invention stems from observation of the inventors that dogs refused to eat herring gull (*Larus argentatus*) eggs, regardless of whether the eggs were cooked or raw. Of twelve dogs (a boston terrier, a labrador retriever, two golden retrievers, a cocker spaniel, a beagle, an airedale and several mixed breed dogs) presented herring gull and chicken (*Gallus callus*) eggs, most refused to consume herring gull eggs and those that did exhibit consumption only ate small amounts with reluctance. Conversely, all readily consumed chicken eggs. Most of the dogs rejected the herring gull eggs prior to sampling them, suggesting that repellency was mediated by a volatile cue. These observations led us to the hypothesis that the herring gull eggs might contain volatile(s) which, if identified, might have practical use as a dog repellent. These volatiles may be present in the eggs of herring gulls, a ground-nesting species, as a natural defense against canine predation. Since cooked eggs were as repellent as raw eggs, it is believed that the repellent may be heated without loss of effectiveness.

To determine whether differences existed between the volatiles present in herring gull and chicken eggs, the headspace above samples of each were individually collected using Tenex filled collection tubes according to methods previously published (Kostelc, J. G., P. R. Zelson, G. Preti, and J. Tonzetich, "Quantitative differences in volatiles from healthy mouths and mouths with periodontitis", *Clinical Chemistry*, 27:842–845, 1981; Preti, G., J. N. Labows, J. G. Kostelc, S. Aldinger, and R. Daniele, "Analyses of lung air from patients with bronchogenic carcinoma and controls using gas chromatography/mass spectrometry", *J. Chromatography*, 432: 1–11,1988). Analyses of the collected constituents were performed using gas chromatography/mass spectrometry (GC/MS).

The volatile components collected from both types of eggs gave similar gas chromatographic patterns. Due to the similar appearance of the chromatographic traces, the mass spectra of individual components from each sample had to be examined.

Examination of the mass spectra showed that herring gull eggs (FIG. 1a) and chicken eggs (FIG. 1b) qualitatively differed in the area designated by the rectangles shown in those figures. These area are expanded in FIGS. 2a and 2b. A variety of different compounds were seen in this small portion of the chromatogram. The shaded compounds found in the herring gull eggs did not, however, appear in the chicken eggs. The mass spectra of the individual components eluting under these shaded peaks as well as the gas chromatographic retention times suggested the following structures: pulegone, $C_{10}H_{16}O$ (eluting in the peak centered at 1603); the second compound eluting at 1710 scans appears to be 3-methyl-5, 5-dimethylcyclohexanone; and the largest component eluting under the peak at 1723 scans appears to be piperitone.

To behaviorally test whether the compounds identified in herring gull eggs were repellent to dogs, two kinds of assay were performed. For the first, ten dog owners were given vials, five of which contained d-pulegone, and five of which contained distilled water. All dogs in this test were mixed breeds. Owners were instructed to take the vials home, and to apply 2.0 microliters of vial contents to their pet's favorite food. The food was then offered to the dogs, and the owners recorded the pets' responses. Owners were not informed as to the contents of the vials provided to them. In all five cases in which pulegone was applied to food, strong rejection was reported. Conversely, when water was applied to food, it was readily accepted.

For the second behavioral assay, forty male beagles were given food paired with the odor of d-pulegone diluted in ethyl alcohol versus food paired with the odor of ethyl alcohol only. Pairing was accomplished by applying 1 ml of 0.2% d-pulegone solution in 1 ml of ethyl alcohol to filter paper disks, and placing these disks beneath samples of familiar diet in two metal bowls. The bowls were presented to the dogs by an observer that did not know which contained the d-pulegone solution disk or which contained the ethyl alcohol disk. Results are presented in Table 1. Of the forty dogs, ten refused to approach either sample. Of the remaining thirty dogs, 73% showed strong rejection of d-pulegone, while the remaining 27% exhibited rejection responses towards the control dish.

TABLE 1

| Not Responsive to Either Sample: | 10 |
| --- | --- |
| Repelled by 0.2% d-Pulegone: | 22 |
| Repelled by 100.0% EtOH: | 8 |

Differences in rejection between d-pulegone and EtOH were significant ($P<0.01$).

It is concluded from the results of these behavioral tests that pulegone and piperitine are effective repellents for dogs. The isomer d-pulegone may have increased efficacy versus other isomers or a racemic mixture. Because a variety of breeds were tested, it is further believed that repellent effects are general, and not specific to only one or a few breeds. In addition, these test results suggest that the substances would be effective repellents for a wide number of carnivorous or omnivorous animals and birds.

What is claimed is:

1. A method of repelling carnivorous or omnivorous animals selected from the group consisting of domestic cats, rodents, raccoons and canids comprising applying to the locus from which said animals are to be repelled an effective repellent amount of one or more volatile compounds selected from the group consisting of pulegone and piperitone.

2. The method of claim 1 where said one or more volatile compounds have a mint-like odor.

3. The method of claim 1 where said volatile compound is pulegone.

4. The method of claim 3 where said volatile compound is d-pulegone.

5. The method of claim 1 where said volatile compound is piperitone.

6. The method of claim 1 where said one or more volatile compounds are substantially non-toxic to mammals.

7. The method of claim 1 where said animal is a canid.

8. The method of claim 1 where said animal is a dog.

9. The method of claim 3 where said animal is a canid.

10. The method of claim 3 where said animal is a dog.

11. The method of claim 4 where said animal is a dog.

12. The method of claim 1 where said locus is trash receptacles.

13. The method of claim 1 where said locus is a poison.

14. The method of claim 13 where said poison is an antifreeze composition.

15. The method of claim 1 where said volatile compound is incorporated into a plastic trash receptacle.

16. The method of claim 15 where said volatile compound is selected from the group consisting of pulegone and piperitone.

17. The method of claim 4 where said animal is a canid.

18. The method of claim 5 where said animal is a canid.

19. The method of claim 18 where said animal is a dog.

* * * * *